United States Patent [19] [11] 4,208,130
Saconney et al. [45] Jun. 17, 1980

[54] METHOD AND APPARATUS FOR OPTICALLY DETECTING DEFECTS IN A TRANSPARENT OBJECT

[75] Inventors: Jean E. Saconney, Paris; Theodore Caloyannis, Courbevoie, both of France

[73] Assignee: Societe Generale pour l'Emballage, Paris, France

[21] Appl. No.: 871,096

[22] Filed: Jan. 20, 1978

[30] Foreign Application Priority Data

Jan. 25, 1977 [FR] France ............... 77 01963

[51] Int. Cl.$^2$ ............... G01N 21/02
[52] U.S. Cl. ............... 356/428; 209/526; 356/240
[58] Field of Search ............... 356/239, 200, 428; 209/526, 538

[56] References Cited
U.S. PATENT DOCUMENTS

| 2,902,151 | 9/1959 | Miles et al. | 356/428 X |
| 3,171,033 | 2/1965 | Mathias et al. | 356/428 |
| 3,249,224 | 5/1966 | Uhlig | 209/526 |
| 3,848,742 | 11/1974 | Krenmayr | 356/428 X |
| 3,887,285 | 6/1975 | Fry et al. | 209/526 |

FOREIGN PATENT DOCUMENTS

| 1377652 | 9/1964 | France | 356/240 |
| 1517766 | 2/1968 | France | 356/240 |
| 995213 | 6/1965 | United Kingdom | 356/240 |

Primary Examiner—John K. Corbin
Assistant Examiner—Matthew W. Koren
Attorney, Agent, or Firm—Pennie & Edmonds

[57] ABSTRACT

An optical control unit comprises a base and at least one optical assembly having optical emitting means and conjugate optical receiving means with preset and fixed focal distances, the optical emitting means and conjugate optical receiving means being associated with the base so as to have fixed orientations with respect to the base and be capable of movement in directions parallel and transverse to the face of the base. The optical control unit is positioned with respect to the object to be inspected, and the optical emitting means and conjugate optical receiving means are sighted on a selected region of the wall of the object, the adjustment of sighting being accomplished through simple translations of the optical emitting means and receiving means while maintaining their orientations on the optical control unit unchanged. The selected region of the wall is scanned through a complete rotation of the object, the deviation in intensity of light collected in the course of this scanning being used to detect defects in the object.

22 Claims, 7 Drawing Figures

METHOD AND APPARATUS FOR OPTICALLY DETECTING DEFECTS IN A TRANSPARENT OBJECT

BACKGROUND OF THE INVENTION

The present invention pertains to a method and apparatus for optically detecting defects in transparent objects, making it possible, through automatic sorting, to eliminate objects which have such defects from the production line.

The invention relates generally to operations in which each transparent object to be inspected is made to stop at one or more successive control stations. At each control station, comprising one or more optical control units, one or more light beams are projected on selected regions of the wall of the object. At the passage of said beams at the wall of the object the light which would be transmitted along set directions is collected. The object is placed in rotation with respect to the control unit, each selected region of the revolving wall of the object being scanned through at least one complete rotation. The deviation in intensity of light collected in the course of this scanning is used to detect the possible presence of certain types of defects and bring about the elimination of objects containing such defects.

The invention pertains more particularly to the detection of defects in objects made of glass, i.e., containers such as bottles, flasks or pots. The defects may be of the type known as glazings in the hollow glass industry. Such glazings, which appear as faults several millimeters long, generally result from a break caused by internal stresses, can involve the entire thickness of the glass wall and have highly varied inclinations.

It is known that such glazings are more likely to appear where there is a variation in form or section of the glass object, and are therefore found especially in the upper parts of containers. Substantially vertical glazings form on the edge of the container, while substantially horizontal glazings form along the flanges, rims or threads. Glazings which form at the shoulder of the container often have the shape of a flattened V.

In the various known optical control processes and devices adjustment of the position of the light emitting and receiving means is generally time consuming, delicate, difficult to reproduce and therefore not very reliable. In practice various optical emitting and receiving means for checking differently shaped objects are attached to swiveling arm support consoles mounted on a common base. This is done to avoid exceedingly costly operations which would result from the use of separate control heads to check differently shaped objects. Adjustment is generally accomplished by successive approximations, the operator responsible for the control looking first, by visual examination, for objects which have defects to be detected, and then setting up the various light emitting means and conjugate receiving means at control stations.

This work is difficult if only because the operator has to function with very low surrounding illumination in order to perceive the light beams. Moreover, because several controls for detecting different types of defects must be effected simultaneously at a single station for reasons of economy, the operator has to avoid interference between the various light beams. The procedures involved are therefore quite delicate, and even when using highly qualified personnel, it is difficult to insure the reproducibility of the settings on separate production runs for a given type of object. Moreover, there are substantial and costly losses of time at each change of production operation.

French Pat. No. 1,588,308 has introduced a significant improvement as concerns these operations by suggesting, in order to eliminate interference between the various light beams and the background noises of internal or external origin such as, for example, variations in the surrounding luminosity, that the light from each optical emitting means on a given control head be given a different modulation, the amplifiers associated with the conjugate optical receiving means being tuned to the modulation of the light to be collected.

It is an object of the present invention to surmount the drawbacks associated with the adjustment of known optical detection processes and devices, by imparting a great ease of application and high degree of reliability and reproducibility to the optical detection of defects in transparent objects. This is accomplished by assigning to each of the various optical emitting means designed to control a given type of defect, and to each of the optical receiving means conjugate therewith, a given orientation and localization previously defined only as a function of the location of the areas to be controlled.

Through tests using statistical analyses to compare the results of direct visual controls and controls obtained using the above-described methods on objects having highly varied shapes and sizes, it has been determined that the installation of the various optical emitting and receiving means required can be standardized and directly related to the shape and size of the object to be inspected.

SUMMARY OF THE INVENTION

In accordance with the present invention an optical control unit is positioned with respect to the object to be inspected or controlled. The optical control unit includes a base and at least one optical assembly of optical emitting means and conjugate optical receiving means having preset and fixed sighting or focal distances. The orientations of the optical emitting means and optical receiving means with respect to the base of the optical control unit are also preset for each type of control considered and maintained constant or fixed. Each optical emitting means and its conjugate optical receiving means are sighted to focus on a selected region of the wall of the object at points opposite each other on the internal and external surfaces of the wall. Light beams are thereby projected on the wall of the object and, at their passage at the wall, light which would be transmitted along set directions is collected. The adjustment of this sighting to focus on the area to be controlled is accomplished through simple translations of the optical emitting means and its conjugate optical receiving means while maintaining their orientations on the optical control unit unchanged. The object is rotated with respect to the optical control unit, and the selected region or regions of the wall are scanned through at least one complete rotation of the object. The deviation in intensity of light collected in the course of this scanning is used to detect defects in the object.

In accordance with a preferred embodiment the point on which a particular optical emitting or optical receiving means is sighted to focus is always located in the same plane, all translation of the given emitting or receiving means which make it possible to effect the sighting adjustments therefore being carried out in directions in or parallel to this previously chosen examination plane. It is convenient that this plane be a radial plane, i.e., one containing the axis of rotation of the object under control. As a result, the angles formed at the focal point by the light beams with this radial examination plane on the one hand, and with the plane perpendicular to the axis of rotation on the other hand, are invariable.

For convenience and standardization of adjustments, the illumination and observation corresponding to the overall examination of a given type of defect by an optical emitting means and its conjugate optical receiving means should be effected in a single radial plane. That is, the radial examination plane for a given optical emitting means and the radial examination plane for its conjugate optical receiving means should be one and the same plane, the adjustment of sighting for such conjugated optical emitting and receiving means being effected by a series of translations of said means along two perpendicular directions parallel to this radial examination plane.

As already noted, an optical emitting means and its conjugate optical receiving means are sighted on two points positioned opposite each other on the surface of the wall of the object, separated only by the thickness of the wall in that area. It is preferable that the optical emitting means be sighted to focus on the internal surface of the wall, and the conjugate optical receiving means be sighted to focus on the external surface of the wall, incident rays penetrating through the internal surface and the detection of rays sent back by the defect occurring on the external surface.

In the description of the invention here presented, the base of the optical control unit is assumed to be stationary, the object to be inspected being put into rotation in a conventional manner by appropriate drive means. Moreover, the axis of rotation of the object is assumed to be vertical. These assumptions are made for reasons of convenience of language and because they correspond to the most currently used mode of application, but they should not in any way be interpreted to limit the scope of the invention.

In practice, the first phase of adjustment, which can be effected a priori on the apparatus, consists in correctly positioning the base of the optical control unit above the object to be inspected. This is accomplished with respect to the axis of rotation of the object and a given base level, corresponding, for example, to the bearing of the bottom or the plane of the edge of the object. The second phase of adjustment, peculiar to each of the optical emitting means and optical receiving means associated with the base of the optical control unit, is carried out after the sighting points corresponding to the area of examination for a given defect have been chosen. This adjustment is advantageously decomposed into two translations of a given emitting or receiving means; a translation parallel to the axis of rotation of the object which brings the focal point of the given optical emitting or receiving means to the height corresponding to the level of the area to be inspected, and then a translation perpendicular to the axis directly related to the internal or external diameter of the object at said level which locates the focal point at the required distance from the axis. These two translations define the chosen control point. The adjustments can be carried out without direct sighting by simple setting along the successive paths of translation.

The present invention also pertains to a device for the application of the above-described process.

Such device comprises, at each station, at least one optical control unit, means for supporting the optical control unit in position with respect to the object to be controlled and means for rotating the object with respect to the optical control unit.

The optical control unit comprises a base and at least one optical assembly with an optical emitting means and a conjugate optical receiving means adapted to the type of defect to be detected. The optical emitting means and the conjugate optical receiving means are mounted on rigid support consoles provides with stands which are engaged with guide means on a face of the base so as to fix the orientations of said optical emitting means and conjugate optical receiving means with respect to said guide means or said base, and so as to allow movement of said optical emitting means and conjugate optical receiving means in directions parallel and transverse to the guide means or the face of the base while preventing any change in the orientations of said optical emitting means and conjugate optical receiving means with respect to the base.

The focal distances for each optical emitting means and its conjugate optical receiving means are preset and fixed.

Locating means are advantageously associated with the stands and guide means allowing the setting off of guide marks in relation to the parameters locating the area to be observed on the object being controlled.

It is possible, for example, to use a cylindrical base centered on the axis of rotation of the object being controlled, but it is generally more advantageous that the base be a plate perpendicular to the axis of rotation. The guide means are preferably rectilinear slots on the face of the base. The stand for each rigid support console preferably comprises a threaded rod with two generally flat opposing parallel faces configured and dimensioned for nonrotatable, slidable engagement in one of said slots and fastening means such as nuts sized for reception on the threaded rod. The threaded rod is engaged with one of the rectilinear slots so that it can be moved in the slot without rotating, the fastening means being used to maintain the rod in a direction perpendicular to the face of the base and immobilize the rod on the base at a given level with respect to the axis of rotation of the object and at a desired distance from that axis of rotation.

If the base is a plate perpendicular to the axis of rotation of the object being controlled, since the sighting or focal distances of the various optical emitting means and receiving means used are preset and fixed, the guide means on the plate are preferably positioned so that, taking into account the orientation of the optical means, the examination planes in which displacements of the focusing points of all the optical emitting means and optical receiving means occur intersect along one and the same straight line which, once the plate has been centered with respect to the object to be controlled, coincides with the axis of rotation of the object so that said examination planes are radial planes with respect to said axis.

According to a preferred embodiment, the guide means for a given optical emitting means and its conjugate optical receiving means are positioned parallel to one another so that the corresponding examination planes for said optical emitting means and conjugate optical receiving means are one and the same.

BRIEF DESCRIPTION OF THE DRAWINGS

The invention will now be further described in terms of the principle of adjustment of the optical means and in terms of a number of presently preferred exemplary embodiments with reference to the accompanying drawings in which.

DESCRIPTION OF PREFERRED EMBODIMENTS

Figure 2:
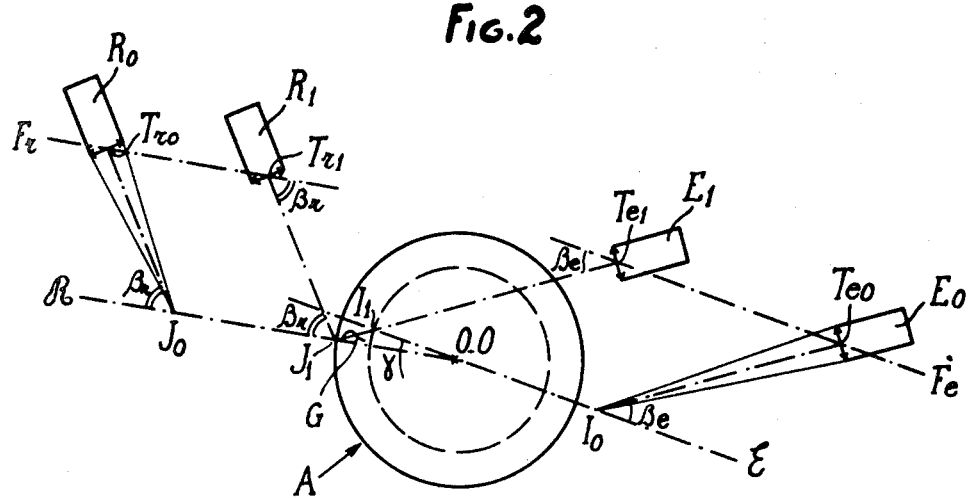
FIGS. 1 and 2 are respectively front and plane diagrammatic views showing positions of the optical emitting means and conjugate optical receiving means in a device according to the invention.
Figure 1:
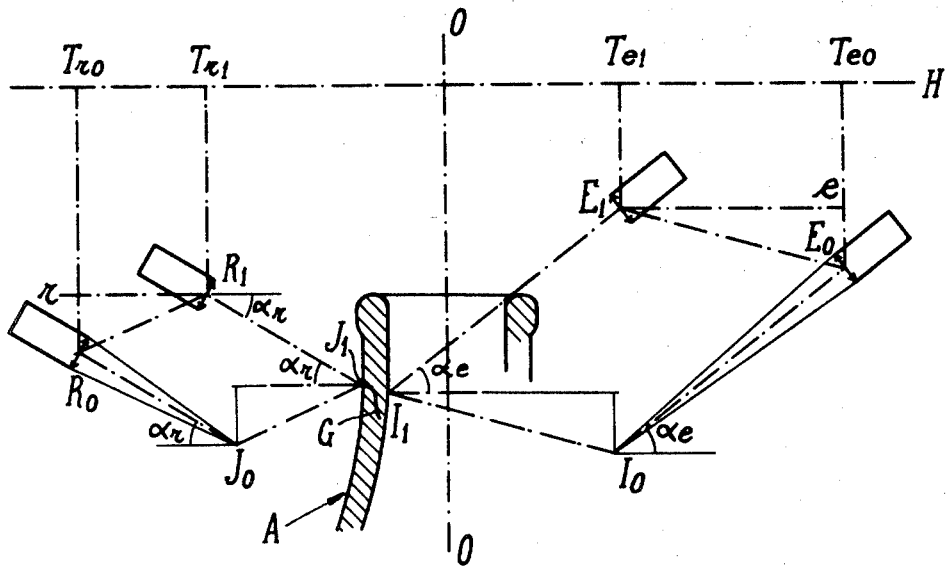

Reference is made first to FIGS. 1 and 2 which show schematically, in accordance with a preferred example, the principle of adjustment of a set of conjugated optical emitting and receiving means according to the invention.

These figures show a flask A having an axis of rotation 0—0 arranged vertically; this flask is put into rotation around its axis under a control unit assumed to be stationary. The flask is put into rotation by a conventional device not shown on this theoretical diagram.

The optical emitting means comprises an emitter E and the conjugate optical receiving means comprises a receiver R. The emitter E and the conjugate receiver R are shown in two distinct positions.

If reference is made, for example, to the position denoted by $E_o$, the orientation of emitter E can be defined by its angle of inclination with respect to a horizontal plane H chosen as a reference plane, i.e., by site angle $\alpha e$ on FIG. 1, by the angle which the vertical plane of the emitter axis forms with radial plane $\mathscr{E}$ passing through the point of convergence $I_o$ of the light beam, i.e., by the azimuth angle $\beta e$ as a horizontal projection on FIG. 2, and, of course, by the position of this radial plane $\mathscr{E}$.

The orientation of receiver R can be identified in an identical manner by means of angles $\alpha r$ and $\beta r$ and the position of radial plane $\mathscr{R}$ which contains point $J_o$ on which the receiver is focused.

In accordance with the invention, the focal distances of emitter E and receiver R are set and fixed as are their orientations in relation to horizontal reference plane H.

Assuming that to effect the control of a certain type of glazing G appearing in an area at a given level of the flask, the choice has been made to illuminate the latter at the level of point $I_1$ on the internal wall in the radial plane $\mathscr{E}$ and to effect the detection at the level of point $J_1$ on the external wall, the corresponding position of emitter E is thus determined by the data of the constant vector $\overrightarrow{I_1E_1} = \overrightarrow{I_oE_o}$ so that it is also possible to write $\overrightarrow{I_oI_1} = \overrightarrow{E_oE_1} = \overrightarrow{E_oe} + \overrightarrow{eE_1}$.

Similarly, with respect to the position of receiver R, $\overrightarrow{J_oJ_1} = \overrightarrow{R_or} + \overrightarrow{rR_1}$.

If, therefore, a condition is imposed on point I whereby it must remain permanently in this radial plane $\mathscr{E}$, it can be seen in FIG. 2 that it is necessary for guiding track $F_e$ for emitter stand $T_e$ on reference plane H to be a segment of a straight line parallel to plane $\mathscr{E}$, at a given distance from axis 0—0 and for the angle of the vertical plane of emitter E with this track to be a constant and equal to $\beta e$. The position of the emitter depends directly on the distance from I to axis 0—0. Similarly, angle $\alpha e$ must remain fixed, the distance to plane H varying with the height of point I.

A similar line of reasoning applies to the displacement of receiver R the stand of which $T_r$ has as its guiding track on plane H a segment of straight line $F_r$ forming an angle $\gamma$ with $F_e$.

It is advantageous in practice to place points I and J in one and the same radial plane with respect to axis 0—0, i.e., to give a zero value to angle $\gamma$ between the two planes $\mathscr{E}$ and $\mathscr{R}$. Under this condition the two guiding tracks $F_e$ and $F_r$ will be parallel. In addition, it is convenient to place point I and J at the same height; although this solution is not always the best adapted from a theoretical point of view to the detection of glazings of a given type, it is sufficient in practice and makes it possible to considerably simplify adjustment data for the various conjugated optical emitting and receiving means.

FIGS. 3 to 7 relate to a control device designed for flasks the necks of which have diameters ranging from 16 to 80 mm.

Figure 3:
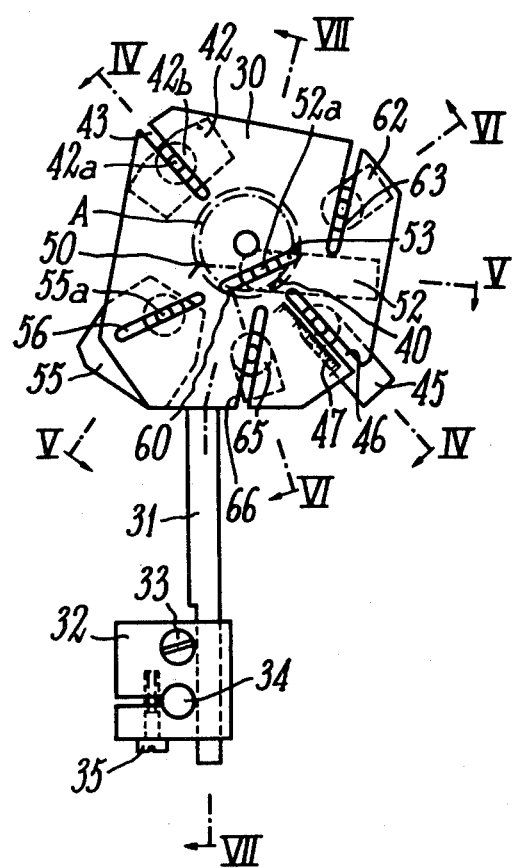
FIG. 3 is a plane view of an optical control station on a device according to the invention.

FIG. 3 illustrates, in plane view and simplified form, the assembly of an optical control unit of one of the stations of an automatic revolving sorting platform. The picture also illustrates part of the support means for said control unit. The optical control unit carries three conjugated optical assemblies corresponding to three different types of controls of which only the support consoles are shown in this figure. These assemblies are shown in more detailed fashion in FIGS. 4 to 7 as front views along the planes of symmetry of each respective emitting unit and conjugate receiving unit.

In FIG. 3 a plate 30 is shown which is mounted at the end part of an arm 31 which slides in a bore in a positioning member such as a nut 32. Locking means such as screw 33 in a threaded aperture in nut 32 allows arm 31 to be secured into place. In like manner, the nut 32 itself slides on a column 34 and can be immobilized by clamping screw 35. In the example shown, column 34 is integral with the general framework of the apparatus and flask A to be controlled is rotated around its axis 0—0 by drive means of a known type; the assembly used to adjust the position of the control plate with respect to flask A is discussed hereafter and illustrated in FIG. 7.

The various optical emitting and receiving groups are movable in slots forming slides which make their individual adjustment possible. As has already been mentioned, the sighting or focal distances of the emitters and receivers is preadjusted and fixed.

Figure 4:
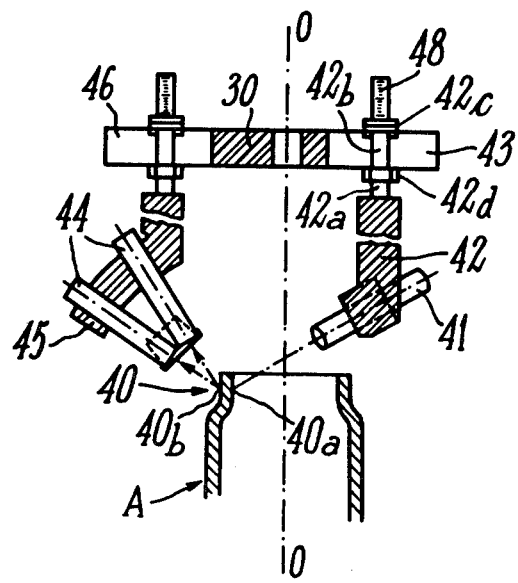
FIG. 4 is a section along IV—IV of FIG. 3.

In FIG. 4, which is a section along IV—IV of FIG. 3, an optical emitting group and conjugate optical receiving group designed to detect horizontal glazings are illustrated. The emitting group comprises two identical emitters 41, only one of which is visible in FIG. 4, mounted at the same inclination along a common console 42. Both emitters 41 are mounted symmetrically and adjusted so that the light beams which they emit converge on the same point. They therefore behave as a single emitter. Console 42 is integral with a threaded rod 42a bearing two generally flat opposing parallel faces 42b. This rod may move without rotating in a slot 43 of plate 30 and can be locked into a vertical position by an assembly of two nuts, one of which 42c makes it possible to adjust the position of console 42 as far as height is concerned and the second of which 42d makes it possible to tighten the console 42 thus immobilizing it at the desired distance from axis 0—0.

The overall adjustment of the optical emitting group thus results from a double translation having a horizontal component and a vertical component.

The receiving group comprises two identical receivers 44 mounted in one and the same vertical plane on a console 45 so that they can be used to observe a point located at a fixed distance from their front lens. The console 45 can be moved and adjusted in a slot 46 of plate 30 in the same way as console 42.

Near each slot is provided a locating means such as scale 47 which can be seen in FIG. 3 for slot 46 only. Similarly, a scale such as 48 makes it possible to locate the height of each emitting or receiving group with respect to plate 30.

In accordance with the explanations given above and as can be seen in FIG. 3, the longitudinal axes of the slots 43 and 46 are along two segments of a straight line aligned in radial plane IV—IV. The focusing of the various emitters and receivers is effected on area 40, on either side of the wall of the flask without any modification of their orientations.

In a manner which is advantageous because of its convenience, the focusing of the emitters and receivers is effected systematically on two points 40a, 40b, placed at the same height, opposite one another, 40a being on the internal surface and 40b being on the external surface of flask A, the emitters illuminating the internal surface. As a result, the graduations of the respective scales indicate directly the distances of points 40a and 40b to axis 0—0, and their height with respect to the reference plane H chosen. Such graduations therefore correspond respectively to the external and internal diameters of flask A in the area to be examined, and the position of that area with respect to the bottom or, preferably, to the edge of the flask.

Figure 5:
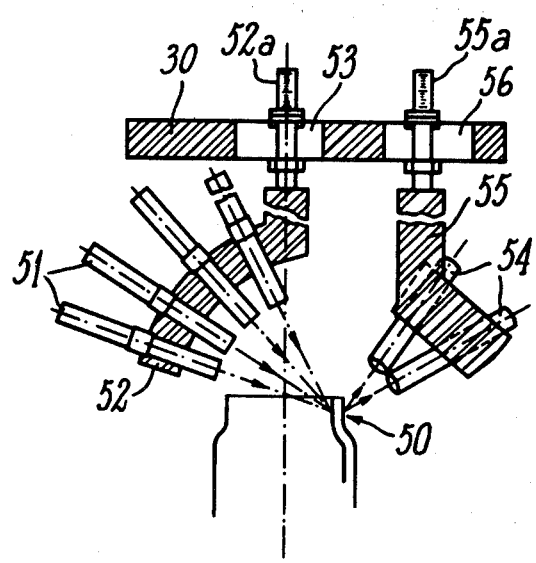
FIG. 5 is a section along V—V of FIG. 3.

In FIG. 5 which is a section along V—V of FIG. 3, an optical emitting group and conjugate optical receiving group designed to detect inclined glazings are illustrated.

The emitting group comprises four identical and converging emitters 51 mounted in the same vertical plane on a common console 52, the rod of which 52a moves in the same manner as described above in a slot 53 of plate 30.

The receiving group comprises four identical and converging receivers 54 which are symmetrical two by two, with respect to the section plane; these receivers, only two of which can be seen in FIG. 5, are mounted on a console 55 the rod of which 55a moves in slot 56. FIG. 3 shows that the longitudinal axes of slots 53 and 56 are aligned so that the displacements of both the emitting and receiving groups at a given level occur along the same straight line. Because of the orientation of the flat parts of rods 52a and 55a, the planes of symmetry of the emitting and receiving groups form a fixed angle so that the focusing occurs on an area 50 in one and the same radial plane parallel to the longitudinal axes of the slots.

Figure 6:
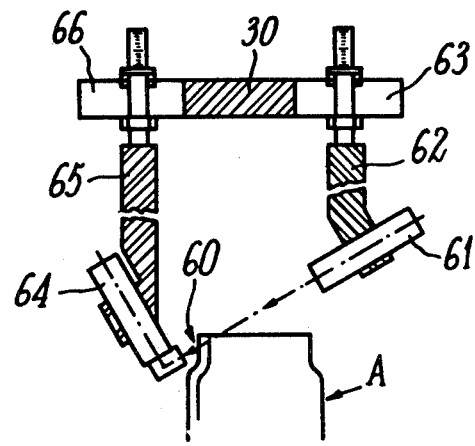
FIG. 6 is a section along VI—VI of FIG. 3.

Reference is now made to FIG. 6 which shows a sectional view along VI—VI of FIG. 3 of the optical emitting means and conjugate optical receiving means providing for the detection of vertical glazings. The emitting means comprises a single emitter 61 mounted on a console 62 the position of which on plate 30 can be adjusted without modifying its orientation using slot 63. The receiving means comprises a single receiver 64 mounted on a console 65 and moving in the same way on plate 30 through a slot 66 parallel to slot 63. The inclination of the optical axis at the inlet of receiver 64 is the reverse of that of emitter 61, i.e., equal but of opposite sign; accordingly, for reasons of convenience, the receiver is provided with a 90° angular member.

The focusing of the emitter and receiver on the area to be controlled 60 is effected in the same way as previously described.

When several controls are to be made simultaneously on an object, the respective positions of the examination planes must be suitably chosen.

Figure 7:
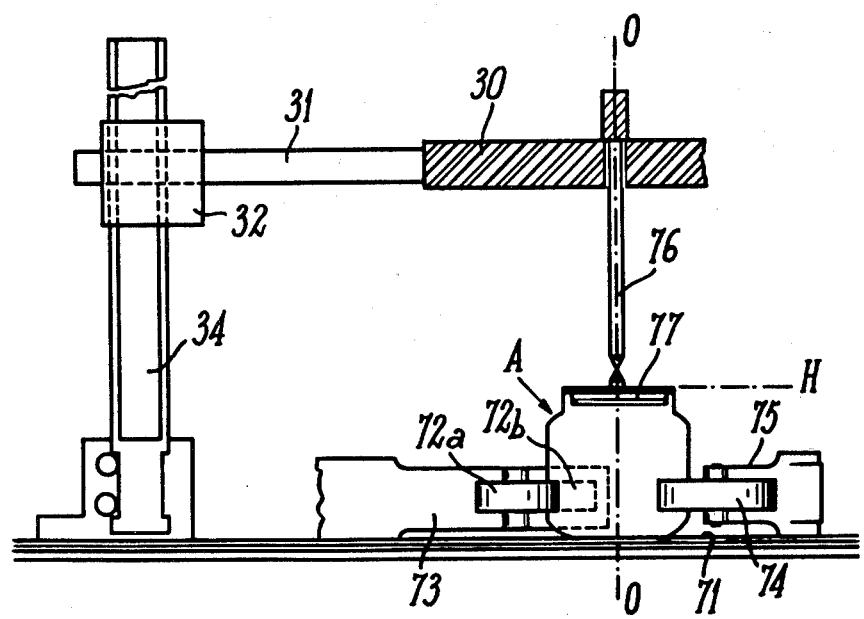
FIG. 7 is a section along VII—VII of FIG. 3.

As was stated hereinabove the plate of the optical control unit of a station is adjusted into set position with respect to the object to be controlled, and the object is rotated by drive means of a known type. With reference to FIG. 7 which is a section VII—VII of FIG. 3, flask A is driven into rotation about its axis 0—0 on platform 71 by two fixed axes rollers 72a and 72b of a transport drum 73 and one drive roller 74 mounted on an elastic restoring member 75, the transport drum 73 and the elastic restoring member 75 being integral with or attached to the platform 71, the drive roller 74 being powered by any conventional means. The position of axis 0—0 depends on the diameter of container A and also on the position of plate 30. One means which can be used to position plate 30 with respect to flask A comprises a centre-punch rod 76 associated with a centering stopper 77. The centre-punch rod is inserted in a centering aperture in plate 30 and the centering stopper is set on an edge of flask A, so that when the centre-punch rod and the centering stopper are aligned, plate 30 is centered over flask A and the height of this plate is set with respect to the edge of the flask before locking it into place with screws 33 and 35 shown in FIG. 3.

A complete control device in accordance with the present invention advantageously comprises a second control station similar to the first with the members mounted symmetrically. The conjugated optical assembly at the second station designed to control horizontal glazings makes it possible to effect a second control at a different height on the flask under inspection; the conjugated optical assembly at the second station designed to control vertical glazings makes it possible to double the control in a given area on the flask, thereby taking into account the fact that such vertical glazings are not necessarily radial, and allowing them to be detected whatever their obliqueness may be; the conjugated optical assembly at the second station designed to control inclined glazings similarly increases control in a given area on the flask and makes it possible to detect these glazings whatever their direction of inclination may be.

In the case where a control is to be effected on an area of an object which does not have a perfect symmetry of revolution, i.e., the ring of a flask having a screw thread, and which therefore gives rise, even in the absence of a defect, to a non-uniform signal, it is useful, in order to reduce the influence of this interfering signal, to place a small diaphragm provided with a rectangular slit on the forward face of the receiver. This can be oriented when adjustment of the receiver is effected in order to improve the signal-noise ratio so as to avoid improper trigger actions of the sorting installation evacuation signal.

In accordance with the present invention, emitters of substantially monochromatic infrared light with a wavelength in the order of 0.9 $\mu$m (infrared diodes) can be used in association with receivers having their maximum sensitivity for this wavelength. In order to avoid any interference due to the superposition of several controls, provision is made in a manner known per se for the modulation of the supply to the emitters at various frequencies and for the amplification of the signals received by the conjugate receivers tuned to the corresponding frequency.

In a specific example of operation of the invention described herein, emitters are arranged to form their images on the internal surface of the wall of the flask 60 mm. away from their front lenses; the receivers being arranged so as to sight points located on the external surface of the wall of the flask 30 mm. away from their front lenses; except for the receivers providing for the detection of vertical glazings. Since the latter receivers comprise angular members which introduce additional optical paths, these receivers are arranged to sight a point on the external surface of the wall of the flask at a distance reduced to 21 mm. from their front lenses.

The focusing is effected on a rectangular image 0.8×7 mm., except as regards the devices providing for the detection of glazings on the shoulder where focusing is effected on an image 2.5×10 mm., since these glazings, which in general are horizontal, can nevertheless have the shape of a flattened V.

In the example described, the assembly of emitters is modulated at a frequency of 7.5 kHz and the corresponding receivers are tuned to that frequency except for the emitter designed to detect vertical glazings and for the conjugate receiver which are adjusted to a frequency of 5 kHz. At the second station, the frequencies can be inverted so that the total number of feeds will be the same for the two channels.

The Table shown below gives the values of the various angles $\alpha e$, $\alpha r$, $\beta e$, $\beta r$, for each of the emitters and receivers of the above-described device. The signs indicated correspond to the orientations shown in the figures. The Table also shows the values for these same angles for a control device designed for containers having diameters ranging from 5 to 25 mm. Since this device is of a design similar to the device already illustrated, it has not been shown.

While the invention has been described hereinabove in terms of a number of presently preferred embodiments of the apparatus thereof, and in terms of presently preferred modes of practice of the method thereof, the invention itself is not limited thereto but rather comprehends all modifications of and departures from those embodiments and modes properly falling within the scope of the appended claims.

We claim:
1. Apparatus for optically detecting defects in a transparent object which comprises:
   a. at least one optical control unit which includes
      i. a base,
      ii. guide means on a face of the base,
      iii. at least two rigid support consoles,
      iv. at least one optical assembly comprising optical emitting means and conjugate optical receiving means having preset and fixed focal distances, the optical emitting means being mounted on one of the rigid support consoles, the optical receiving means being mounted on another of the rigid support consoles,
      v. a stand for each rigid support console, engaged with the guide means so as to set and fix the orientation of the associated optical emitting or receiving means with respect to the base and so as to allow movement of the associated optical emitting or receiving means in directions parallel and transverse to the face of the base while preventing any change in the orientation of the associated optical emitting or receiving means with respect to the base, the guide means being positioned on the face of the base so that on movement of the optical emitting means and conjugate optical receiving means all displacements of the points of focus of the optical emitting means and conjugate optical receiving means are confined to a single examination plane;
   b. means for supporting the optical control unit in position with respect to the object; and
   c. means for rotating the object with respect to the optical control unit.

2. The apparatus of claim 1 in which there are at least two of said optical assemblies and the guide means are positioned on the face of the base so that the examination planes for the optical emitting means and conjugate optical receiving means of all of said optical assemblies cross along one straight line which coincides with the axis of rotation of the object, all of said examination planes being radial planes with respect to the axis of rotation of the object.

3. The apparatus of claim 2 in which the base is a plate with a face perpendicular to the axis of rotation of the object.

| | | | Optical definition of Emitter-Receiver positionings | | | | | | | | | | | | |
|---|---|---|---|---|---|---|---|---|---|---|---|---|---|---|---|
| | | | Control Device For Containers Having Diameters Ranging From 16 to 80 mm | | | | | | | Control Device For Containers Having Diameters Ranging From 5 to 25 mm | | | | | |
| | | | Emitters | | | | Receivers | | | | Emitters | | Receivers | | | |
| | | | 1 | 2 | 3 | 4 | A | B | C | D | 1 | 2 | A | B | C | D |
| Vertical Glazings | | $\alpha e$ | 30° | | | | $\alpha r$ | −30° | | | | 35° | | $\alpha r$ | −35° | | |
| | | $\beta e$ | 40° | | | | $\beta r$ | 30° | | | | 47° | | $\beta r$ | 20° | | |
| Inclined Glazings | high | $\alpha e$ | 18° | 30° | 45° | 60° | $\alpha r$ | 33° | 57° | 57° | 33° | 30° | 45° | $\alpha r$ | 40° | 40° | |
| | | $\beta e$ | 30° | 30° | 30° | 30° | $\beta r$ | 6° | 17° | 45° | 54° | 0° | 0° | $\beta r$ | +38° | −38° | |
| | low | $\alpha e$ | | | | | $\alpha r$ | | | | | 30° | 45° | $\alpha r$ | 35° | 35° | |
| | | $\beta e$ | | | | | $\beta r$ | | | | | 0° | 0° | $\beta r$ | +53° | −53° | |
| Horizontal Glazings | high | $\alpha e$ | 30° | 30° | | | $\alpha r$ | 33° | 57° | | | 50° | 50° | $\alpha r$ | 45° | | |
| | | $\beta e$ | +12,5° | −12,5° | | | $\beta r$ | 0° | 0° | | | +30° | −30° | $\beta r$ | 0° | | |
| | low | $\alpha e$ | 30° | 30° | | | $\alpha r$ | 33° | 57° | | | 50° | 62° | $\alpha r$ | 23° | 48° | 23° | +27° |
| | | $\beta e$ | −12,5° | −12,5° | | | $\beta r$ | 0° | 0° | | | 0° | 0° | $\beta r$ | −27° | −27° | +27° | +27° |
| Shoulder Glazings | | $\alpha e$ | | | | | $\alpha r$ | | | | | 60° | | $\alpha r$ | 40° | 40° | |
| | | $\beta e$ | | | | | $\beta r$ | | | | | 0° | | $\beta r$ | −17° | +17° | |
| Body Glazings | | $\alpha e$ | 0° | | | | $\alpha r$ | 0° | | | | 0° | | $\alpha r$ | 0° | | |
| | | $\beta e$ | 40° | | | | $\beta r$ | 35° | | | | 40° | | $\beta r$ | 35° | | |

4. The apparatus of claim 3 in which the guide means are a plurality of rectilinear slots on the face of the plate and each stand comprises a threaded rod with two generally flat opposing parallel faces configured and dimensioned for nonrotatable, slidable engagement in one of the rectilinear slots and fastening means, the threaded rod being engaged with one of the rectilinear slots so that it can move in the slot without rotating, the fastening means maintaining the rod in the slot in a direction perpendicular to the face of the plate and immobilizing the rod at a given level with respect to the axis of rotation of the object and at a desired distance from said axis of rotation.

5. The apparatus of claim 4 in which said fastening means are nuts sized for reception on the threaded rod.

6. The apparatus of claim 4 in which the rectilinear slots and threaded rods are provided with locating means.

7. The apparatus of claim 6 in which said locating means are scales marked on the plate alongside the rectilinear slots and on the threaded rods.

8. The apparatus of claim 2 in which the optical emitting means of one of said optical assemblies emits light modulated at a set frequency, its conjugate optical receiving means being tuned to the set frequency, and the optical emitting means of another of said optical assemblies emits light modulated at a different set frequency, its conjugate optical receiving means being tuned to the different set frequency.

9. The apparatus of claim 1 in which the support means comprises a platform, a column integral with the platform, a positioning member slidably attached to the column, a first locking means for securing the position of the positioning member with respect to the column, an arm slidably attached to the positioning member and having mounted at one end the base of the optical control unit, and a second locking means for securing the position of the arm with respect to the positioning member.

10. The apparatus of claim 9 in which the first and second locking means are screws and the positioning member is a nut with bores for receiving the column and the arm and threaded apertures for receiving the screws.

11. The apparatus of claim 9 in which the means for rotating the object comprises a transport drum integral with the platform, two fixed axes rollers attached to the transport drum for contacting and guiding the object, an elastic restoring member integral with the platform, and a drive roller attached to the elastic restoring member for contacting, guiding and driving the object in rotation.

12. The apparatus of claim 9 in which the base of the optical control unit has a centering aperture located at a point which is to be centered over the object, and the apparatus further comprises a centre-punch rod for insertion in the centering aperture and a centering stopper for fitting on an edge of the object so that the centre-punch rod and the centering stopper can be aligned to center the optical control unit with respect to the object.

13. The apparatus of claim 1 in which the optical emitting means comprises at least one emitter and the optical receiving means comprises at least one receiver.

14. The apparatus of claim 13 in which the emitter and receiver use infrared light having a wavelength of 0.9 μm.

15. The apparatus of claim 1 in which the optical emitting means comprises two identical and converging emitters mounted symmetrically at the same inclination and the conjugate optical receiving means comprises two identical converging receivers mounted in the vertical plane of symmetry of said emitters.

16. The apparatus of claim 1 in which the optical emitting means comprises four identical and converging emitters mounted in the same vertical plane and, the conjugate optical receiving means comprises four identical and converging receivers mounted symmetrically two by two with respect to another vertical plane.

17. The apparatus of claim 1 in which the optical emitting means comprises an emitter and the conjugate optical receiving means comprises a receiver having an optical axis with an inclination which is the reverse of the inclination of said emitter.

18. The apparatus of claim 17 in which the optical receiving means further comprises a 90° angular member attached at the inlet of the receiver.

19. The apparatus of claim 1 in which at least one of the optical receiving means comprises a receiver and a diaphragm with a rectangular slit which covers the forward face of the receiver for detecting defects in an area of the object which does not have a perfect symmetry of revolution.

20. Method for optically detecting defects in a transparent object which comprises:
  a. positioning an optical control unit with respect to the object, the optical control unit comprising at least one optical assembly including optical emitting means and conjugate optical receiving means, said optical emitting means and conjugate optical receiving means each having a preset and fixed focal distance and a preset and fixed orientation on the optical control unit;
  b. rotating the object with respect to the optical control unit;
  c. sighting said optical emitting means and conjugate optical receiving means to focus on selected regions of the wall of the object at points opposite each other on the internal and external surfaces of the wall so that one or more light beams are projected on the wall and, at the passage of said beams at the wall, light which would be transmitted along set directions is collected, said sighting comprising translating said optical emitting means in a direction parallel to the axis of rotation of the object and in a direction perpendicular to said axis of rotation while maintaining the orientation of said optical emitting means unchanged and confining displacements of its point of focus to a single examination plane containing said axis of rotation and translating said conjugate optical receiving means in a direction parallel to said axis of rotation and in a direction perpendicular to said axis of rotation while maintaining the orientation of said conjugate optical receiving means unchanged and confining displacements of its point of focus to said single examination plane; and
  d. scanning selected regions of the wall of the object through at least one complete rotation of the object, the deviation in intensity of light collected in the course of the scanning being used to detect defects in the object.

21. The method of claim 20 wherein said optical emitting means is sighted to focus on the internal surface of the wall of the object and said conjugate optical receiving means is sighted to focus on the external surface of the wall of the object, incident light beams penetrating through said internal surface, light which would be transmitted being detected on said external surface.

22. Apparatus for optically detecting defects in a transparent object which comprises an optical control unit comprising optical emitting means and conjugate optical receiving means having preset and fixed focal distances, means for supporting the optical control unit in position with respect to the object, and means for rotating the object with respect to the optical control unit, the optical emitting means being associated with the support means for the optical control unit so as to set and fix the orientation of the optical emitting means and so as to allow movement of the optical emitting means in a direction parallel to the axis of rotation of the object and in a direction perpendicular to said axis of rotation while maintaining the orientation of the optical emitting means unchanged and confining displacements of its point of focus to a single examination plane containing said axis of rotation, the conjugate optical receiving means being associated with the support means for the optical control unit so as to set and fix the orientation of the conjugate optical receiving means and so as to allow movement of the conjugate optical receiving means in a direction parallel to said axis of rotation and in a direction perpendicular to said axis of rotation while maintaining the orientation of the conjugate optical receiving means unchanged and confining displacements of its point of focus to said single examination plane containing said axis of rotation.

* * * * *

UNITED STATES PATENT AND TRADEMARK OFFICE
CERTIFICATE OF CORRECTION

PATENT NO. : 4,208,130
DATED : June 17, 1980
INVENTOR(S) : Jean E. Saconney and Theodore Caloyannis It is certified that error appears in the above-identified patent and that said Letters Patent are hereby corrected as shown below:

Column 4, line 13, after "consoles" and before "with", "provides" should be -- provided --;

In the portion of the Table in Column 9, the datum "-12,5°" in the 10th line under "Emitters 1" should be -- +12,5° --;

In the portion of the Table in Column 10, insert -- 48° -- in the 9th line of the column headed "Receivers D".

*Signed and Sealed this*

*Sixteenth* Day of *September 1980*

[SEAL]

*Attest:*

SIDNEY A. DIAMOND

*Attesting Officer*     *Commissioner of Patents and Trademarks*